United States Patent [19]

Hu

[11] Patent Number: 5,469,487
[45] Date of Patent: Nov. 21, 1995

[54] CT SYSTEM WITH TWIN FAN BEAM HELICAL SCAN

[75] Inventor: Hui Hu, Waukesha, Wis.

[73] Assignee: General Electric Company, Milwaukee, Wis.

[21] Appl. No.: 175,703

[22] Filed: Dec. 30, 1993

[51] Int. Cl.$^6$ .................... A61B 6/03; G01N 23/083
[52] U.S. Cl. ................... 378/9; 378/15; 378/901
[58] Field of Search .................... 378/9, 15, 99

[56] References Cited

U.S. PATENT DOCUMENTS

| | | | |
|---|---|---|---|
| 4,725,963 | 2/1988 | Taylor et al. | 364/507 |
| 5,170,346 | 12/1992 | Crawford et al. | 364/413.16 |
| 5,216,601 | 6/1993 | Crawford et al. | 364/413.16 |
| 5,265,142 | 11/1993 | Hsieh | 378/4 |

OTHER PUBLICATIONS

*Optimization of Short Scan Convolution Reconstruction In Fan Beam CT*, Dept of Radiation Oncology, Univ. of Calif. at San Francisco, 1982, pp. 199–202, Dennis L. Parker.
*Computed Tomography Scanning With Simultaneous Patient Translation*, Med. Phys. 17(6), Nov/Dec 1990, pp. 967–982, Carl R. Crawford, et al.

Primary Examiner—David P. Porta
Assistant Examiner—David Vernon Bruce
Attorney, Agent, or Firm—Quarles & Brady

[57] ABSTRACT

A method of producing a tomographic image from x-ray projection data acquired during a helical scan with two fan beams, includes weighting selected data in each projection data array to account for data redundancy and distance from the image plane. Each weighted array of projection data is back projected and combined to form the desired slice image.

4 Claims, 5 Drawing Sheets

CT SYSTEM WITH TWIN FAN BEAM HELICAL SCAN

BACKGROUND OF THE INVENTION

The present invention relates to computed tomography (CT) imaging apparatus; and more particularly, the reconstruction of images from data acquired during a helical scan using twin fan beams.

In a current computed tomography system, an x-ray source projects a fan-shaped beam which is collimated to lie within an X–Y plane of a Cartesian coordinate system, termed the "imaging plane." The x-ray beam passes through the object being imaged, such as a medical patient, and impinges upon a linear array of radiation detectors. The intensity of the transmitted radiation is dependent upon the attenuation of the x-ray beam by the object and each detector produces a separate electrical signal that is a measurement of the beam attenuation. The attenuation measurements from all the detectors are acquired separately to produce the transmission profile.

The source and the linear detector array in a conventional CT system are rotated with a gantry within the imaging plane and around the object so that the angle at which the x-ray beam intersects the object constantly changes. A group of x-ray attenuation measurements from the detector array at a given gantry angle is referred to as a "view" and a "scan" of the object comprises a set of views made at different gantry angles during one revolution of the x-ray source and detector. In an axial scan, data is processed to construct an image that corresponds to a two dimensional slice taken through the object. The prevailing method for reconstructing an image from a set of data is referred to in the art as the filtered backprojection technique. This process converts the attenuation measurements from a scan into integers called "CT numbers" or "Hounsfield units", which are used to control the brightness of a corresponding pixel on a cathode ray tube display.

In order to reduce total scan time when multiple slices are acquired, a so-called "helical" scan is performed where the patient is moved while the gantry revolves to acquire data for the prescribed number of slices. However, helical scanning introduces certain errors with regard to the data in the acquired tomographic projection sets. The mathematics of tomographic reconstruction assumes that the tomographic projection set is acquired along a constant z-axis slice plane. The helical scan path clearly deviates from this condition and this deviation, if uncompensated, results in image artifacts in the reconstructed slice image. The severity of the image artifacts depends generally on the "helix offset" in the projection data, measured as the difference between the table locations of the scanned data and the z axis value of the desired slice plane. Errors resulting from helical scanning will be referred to collectively as "skew" errors.

Several methods have been used to reduce skew errors in helical scanning. A first approach disclosed in copending U.S. Pat. No. 5,046,003 entitled "Method for Reducing Skew Image Artifacts in Helical Projection Imaging" and assigned to the same assignee as the present invention, uses nonuniform table motion to concentrate the helically acquired projections near the slice plane while limiting the accelerative forces on the patient.

In copending U.S. patent application Ser. No. 07/430,372 filed Nov. 2, 1989 entitled "Computerized Tomographic Image Reconstruction Method for Helical Scanning," and assigned to the same assignee as the present invention, skew artifacts are reduced by interpolating between two half scans of data each requiring only 180° plus the fan beam angle of gantry rotation. The half scans require less gantry rotation and hence less table movement, thereby reducing the overall helical offset of the projection data.

In a third approach described in copending U.S. patent application Ser. No. 07/435,980 filed Nov. 13, 1989 entitled "Extrapolative Reconstruction Method for Helical Scanning," and assigned to the same assignee as the present invention, skew artifacts are reduced by interpolating and extrapolating between two partial projection sets of only 180° of gantry rotation. The two partial projection sets require even less gantry rotation than the above half scan approach and, thereby further reduce the overall helical offset of the projection data. Skew artifacts are further reduced by weighting the acquired data as a function of distance from the slice plane as described in U.S. Pat. No. 5,170,346 entitled "Method For Reducing Patient Translation Artifacts In Tomographic Imaging."

These prior methods produce good images when the patient translation speed is moderate, i.e., not greater than 10 mm per gantry rotation. Further reductions in scan time cannot be achieved by increasing patient translation speed because significant image degradations occur.

SUMMARY OF THE INVENTION

The present invention relates to a CT system in which two fan beams displaced along the axis of gantry rotation acquire projection data during a helical scan. This system can be approximated as two rows of detectors which simultaneously collect projection measurements at different axial locations. When such a system operates in the helical mode, it generates interwoven double helixes, as opposed to a single helix from a conventional fan beam helical scan. The interwoven double helixes mapped out by the two fan beams yields projection data from which images in each prescribed slice may be reconstructed with reduced image degradation due to patient translation. More specifically, projection space data arrays are selected from projection data acquired by each fan beam, data in each array is weighted to correct for the translational motion of the patient and to offset data redundancy affects.

A general object of the intention is to combine data from two fan beams to enable patient table speed to be increased during a helical scan without increasing motion artifacts.

GENERAL DESCRIPTION OF THE INVENTION

Figure 3:
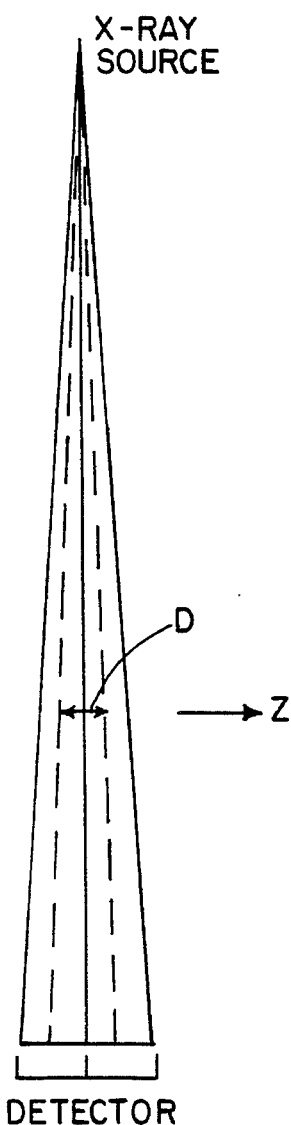
FIG. 3 is a schematic representation of dual, x-ray fan beam in cross section along the z-axis.

As shown in FIG. 3, two rows of detector are employed in a twin fan beam system. The x-ray fan beam is, in effect, split into two fan beams, displaced along the z-axis of rotation. If we denote the two fan beams as the front and back beam, the distance between the center of these two beams is D when measured at the iso-center.

Figure 4:
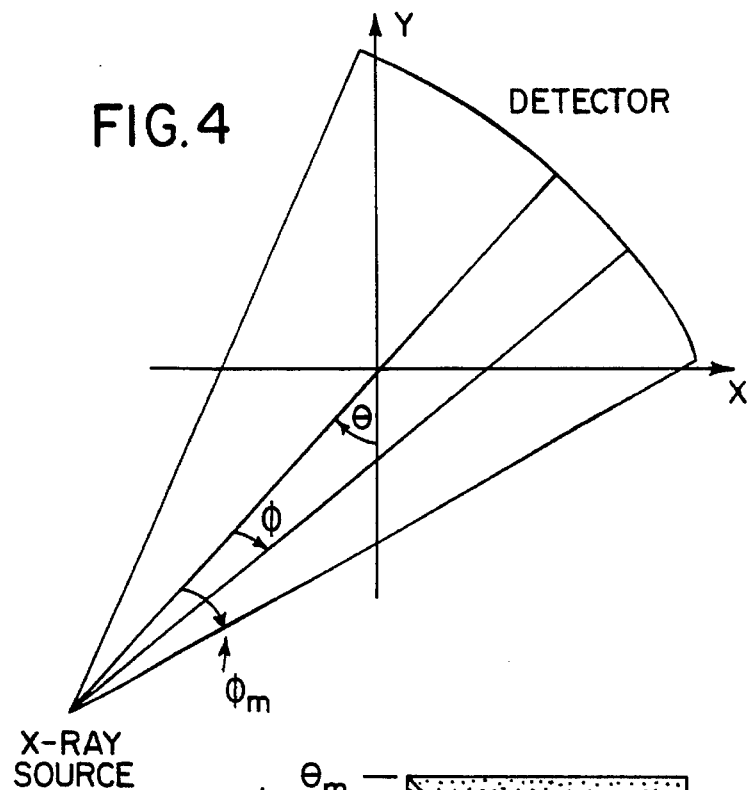
FIG. 4 is a schematic representation of an x-ray fan beam as seen in the imaging plane.

With reference to FIG. 4 the gantry angle is denoted as $\theta$. The detector angles and the view angles of both front and back fan beams can be characterized as $\phi_\pm$ and $\theta_\pm$ respectively, where the view angle of each fan beam is characterized by the corresponding local coordinate that equals zero when the fan beam is at the image position to be reconstructed.

Let the table advancement per gantry rotation be Z, the table's axial position be z and the slice position to be reconstructed be $z_s$. The front and back beam's positions are $z_+$ and $z_-$ respectively. They can be expressed as:

$$z_+ - z_s = k\theta + \frac{D}{2} = k(\theta + p\pi) = k\theta_+ \quad (1a)$$

$$z_- - z_s = k\theta - \frac{D}{2} = k(\theta - p\pi) = k\theta_- \quad (1b)$$

$$\text{where:} \quad k = \frac{Z}{2\pi} \ ; \quad \text{and} \quad p = \frac{D}{Z} \ .$$

Figure 5:
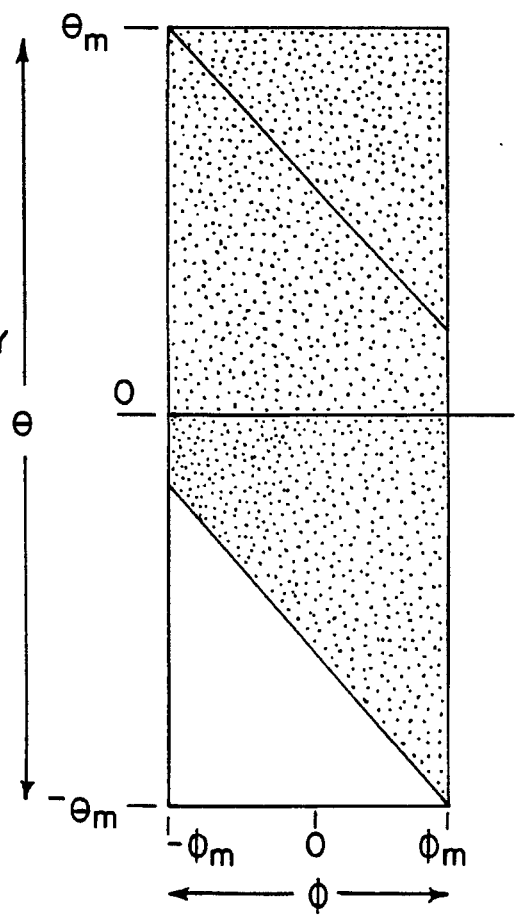
FIG. 5 is a map of a complete set of projection data acquired by a single fan beam.

In helical $Z_\pm$ is a function of $\theta_\pm$, expressed as $Z_\pm(\theta_\pm)$. It is well known that in the absence of the patient motion, a set of fan beam projections collected over $\pi$ radians plus the angle of the fan beam of gantry rotation are sufficient for reconstruction. With reference to FIG. 5, such a projection set can be described in the projection space $(\theta,\phi)$, with $\phi$ in the range $(-\phi_m, \phi_m)$ and $\theta$ in the range $(-\theta_m, \theta_m)$, where $\phi_m$ is half of the fan angle and $\theta_m = \pi/2 + \phi_m$. In theory, the projection data in the shaded region in FIG. 5 is sufficient for reconstruction of an image.

A twin helical scan gives two sets of projection data denoted as, $P_+(\theta_+, \phi_+)$ and $P_-(\theta_-,\phi_-)$. To minimize the slice profile widening in reconstruction, only those projection data from each data set that is centered at $z_s$ and is collected with $\theta_+$ or $\phi_-$ ranging from $-\theta_m$ to $\theta_m$ is used. Such two data sets are depicted in FIG. 6, where the centers of these two data sets are shifted by an amount $\Delta=2p\pi$ in the gantry angle direction due to the displacement of the two detector rows.

Figure 6:
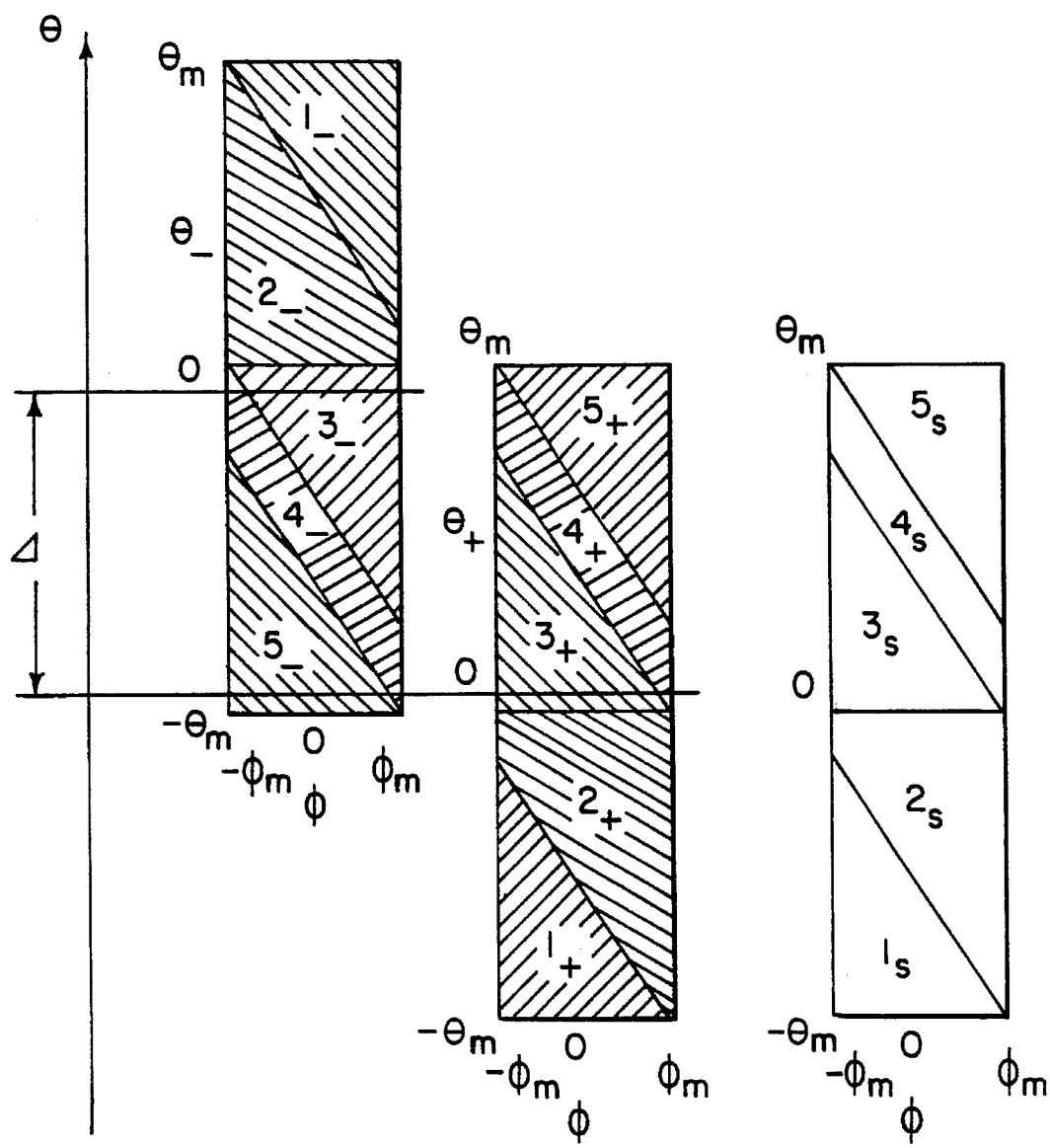
FIG. 6 is a map of projection data acquired by the dual x-ray fan beam of FIG. 3 showing how it is combined to form projection data for a single slice.

The areas of redundant data for the twin fan beam helical projections are similarly striped in FIG. 6 and denoted as $1_+$ to $5_+$ and $1_-$ to $5_-$ respectively. The boundaries between these regions in the two data sets are as follows:

| Boundary | Equation |
|---|---|
| $1_-/2_-$ | $\theta = \theta_m - 2\phi_m - 2\phi$ |
| $2_-/3_-$ | $\theta = -\Delta + \phi_m$ |
| $3_-/4_-$ | $\theta = -\Delta + \theta_m - 2\phi_m - 2\phi$ |
| $4_-/5_-$ | $\theta = -\theta_m + 2\phi_m - 2\phi$ |
| $1_+/2_+$ | $\theta = -\theta_m + 2\phi_m - 2\phi$ |
| $2_+/3_+$ | $\theta = \Delta - \theta_m$ |
| $3_+/4_+$ | $\theta = \Delta - \theta_m + 2\phi_m - 2\phi$ |
| $4_+/5_+$ | $\theta = \theta_m - 2\phi_m - 2\phi$ |

The redundant data may be correctly combined to create a new set of data at the slice position $z_s$ from which an image is reconstructed. The center of the created data set could be anywhere without affecting the result. For convenience, the center is chosen to align with the center of the front beam, as shown in FIG. 6. This new set of data is formed by regions $1_s$ to $5_s$. Note that the regions $2_s$ to $5_s$ form a complete data set from which an image can be reconstructed at the desired slice position.

The data combining process can generally be expressed as:

$$P_s(\theta, \phi, Z_s) = \quad (2)$$
$$w_+(\theta_+, \phi_+)P_+(\theta_+, \phi_+) + w_-(\theta_-, \phi_-)P_-(\theta_-, \phi_-)$$

The weights are given by:

$$w_+(\theta, \phi) = \frac{z_- - z_s}{z_- - z_+} = 1 + \frac{z_+ - z_s}{z_- - z_+} \quad (3)$$

$$w_-(\theta, \phi) = \frac{z_s - z_+}{z_- - z_+} = 1 - \frac{z_- - z_s}{z_- - z_+}$$

With reference to FIG. 6: regions $2_+$ and $2_-$ are combined to obtain region $2_s$; regions $3_+$, $5_-$ and $1_-$ are combined to obtain region $3_s$; regions $4_+$ and $4_-$ are combined to obtain region $4_s$; and regions $3_-$, $5_+$ and $1_+$ are combined to obtain region $5_s$.

Regions $3_s$ and $5_s$ are obtained by combining three redundant measurements. This is done by combining each of two redundant measurements from one data set with the redundant measurement from the other data set using equation (2) to form two combined projections, $P(\theta_1, \phi_2, z_s)$ and $P(\theta_2, \phi_1, z_s)$. Further combine these two combined projections as follows:

$$P_2(\theta_+, \phi_+, z_s) = a(\theta_1, \phi_1) P(\theta_1, \phi_1, z_s) + a(\theta_2, \phi_2) P(\theta_2, \phi_2, z_s) \quad (4)$$

where $(\theta_1, \phi_1)$ and $(\theta_2, \phi_2)$ have the following relation:

$$\theta_2 = \theta_1 + \pi + 2\phi_1 \text{ and } \phi_2 = -\phi_1 \quad (5)$$

Thus, a $(\theta,\phi)$ is actually the halfscan weights which satisfies:

$$a(\theta, \phi) + a(\theta + \pi + 2\phi, -\phi) = 1 \quad (6)$$

With the combining strategy described above, there are two kinds of combinations. One kind includes combining $5_-$ and $3_+$, $4_-$ and $4_+$, and $3_-$ and $5_+$. The rest of the combining forms the other kind. The latter is called the first kind combination while the former is called the second kind combination. For the second kind combination, one has:

$$\theta_- = \theta_+ - \Delta \text{ and } \phi_- = \phi_+ \quad (7a)$$

Thus, from Equations (3) and (1), one then has $$w_{2\pm}(\theta,\phi) = 1 \mp \theta/\Delta \quad (8a)$$

For the first kind combination, one has:

$$\theta_- = \theta_+ - \Delta + \pi + 2\phi_+ \text{ and } \phi_- = -\phi_+ \quad (7b)$$

Similarly, from Equations (3) and (1), one then has $$w_{1\pm}(\theta, \phi) = 1 \pm \frac{\theta}{\pi - \Delta \pm 2\phi} \quad (8b)$$

The resulting combined weights applied to each region of $P_+(\theta, \phi)$ and $P_-(\theta, \phi)$, are:

Region $1_+$: $a_+(\theta, \phi) \, w_{1+}(\theta, \phi)$ (9)
Region $1_-$: $a_-(\theta, \phi) \, w_{1-}(\theta, \phi)$
Region $2_+$: $w_{1+}(\theta, \phi)$
Region $2_-$: $w_{1-}(\theta, \phi)$
Region $3_+$: $a_+(\theta - \Delta, \phi) \, w_{2+}(\theta, \phi) +$
$(1 - a_+(\theta - \Delta, \phi)) \, w_{1+}(\theta, \phi)$
Region $3_-$: $a_-(\theta + \Delta, \phi) \, w_{2-}(\theta, \phi) +$
$(1 - a_-(\theta + \Delta, \phi)) \, w_{1-}(\theta, \phi)$
Region $4_+$: $w_{2+}(\theta, \phi)$
Region $4_-$: $w_{2-}(\theta, \phi)$
Region $5_+$: $a_+(\theta, \phi) \, w_{2+}(\theta, \phi)$
Region $5_-$: $a_-(\theta, \phi) \, w_{2-}(\theta, \phi)$ where: $a_+(\theta, \phi) = a_-(-\theta, -\phi) = a(\theta, \phi)$ (10)

There are many ways of choosing the redundancy weighting $a(\theta, \phi)$. As an example, the following weighting can be used:

$$a(\theta,\phi) = a[x(\theta,\phi)] = 3x^2(\theta,\phi) - 2x^3(\theta,\phi) \quad (11a)$$

where $$x(\theta, \phi) = \begin{cases} \dfrac{\theta + \theta_m}{2\phi_m - 2\phi} & -\theta_m \leq \theta < -\theta_m + 2\phi_m - 2\phi \\ 1 & -\theta_m + 2\phi_m - 2\phi \leq \theta \leq \theta_m - 2\phi_m - 2\phi \\ \dfrac{-\theta + \theta_m}{2\phi_m + 2\phi} & \theta_m - 2\phi_m - 2\phi < \theta < \theta_m \end{cases} \quad (11b)$$

In the above derivation, it is assumed that $\theta_m = \pi/2 + \phi_m$. Since in practice $\theta_m$ can be greater than this value, the derivation of similar equations for such a situation can also be derived.

The projection data in each array $P_+$ and $P_-$ is thus weighted as indicated in equation (9) and then combined to form the desired image at $z_s$. This combination can be done in two ways. The corresponding elements in each properly weighted array can be added together to form the combined projection array which is then filtered and back projected to form the image. In the alternative, each properly weighted array can be separately filtered and back projected to form separate images. The corresponding elements, or pixels, in image space array can be added together to form the final image at $z_s$.

Figure 8:
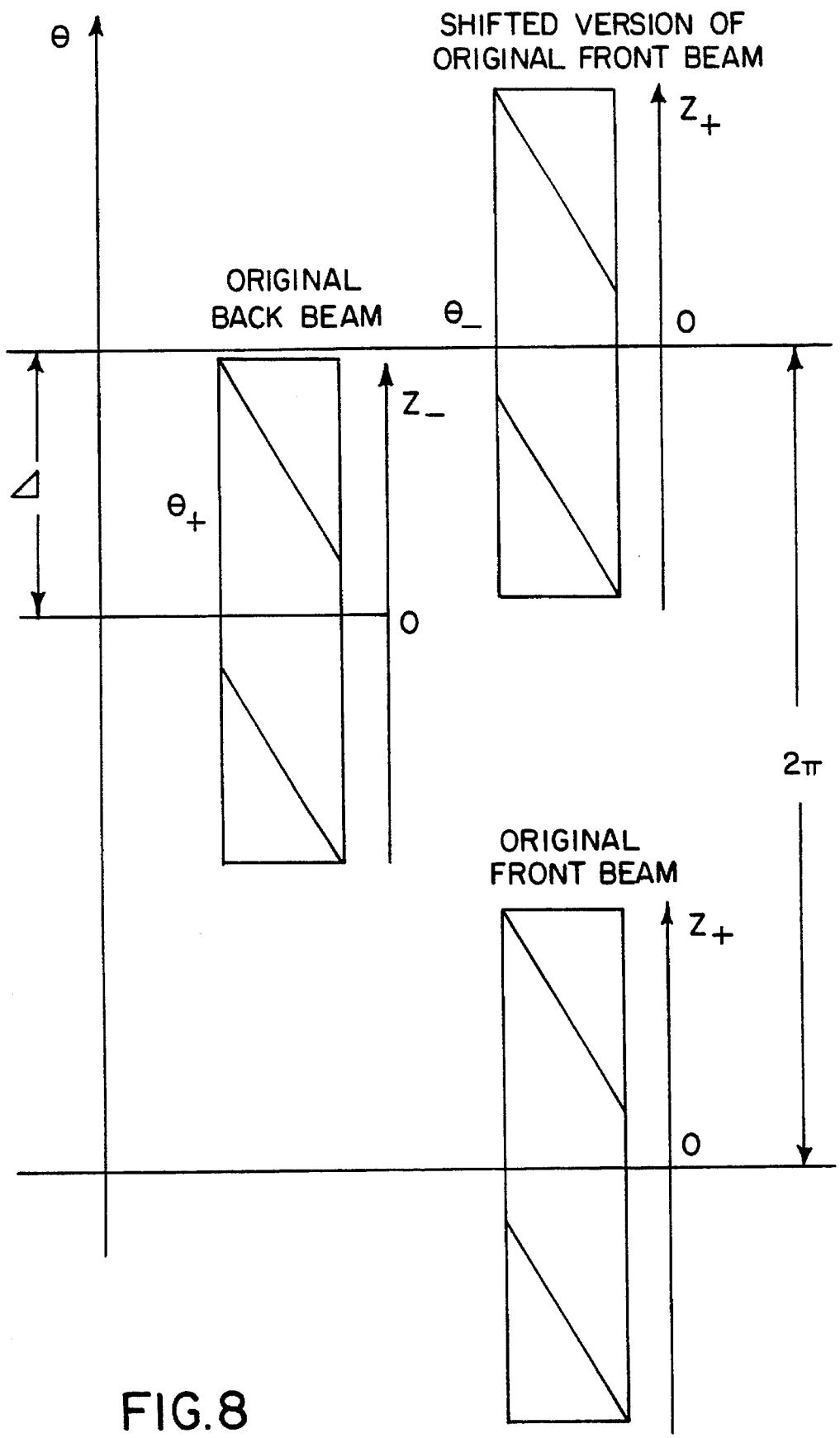
FIG. 8 is a map of projection data acquired when the helical table speed is relatively high.

The invention described above is directly applicable to the case where the helical table speed exceeds a certain speed so that ($p < \frac{1}{2} - \phi_m/\pi$). With the following transformation, it is also applicable to the case where the helical table speed is slower. In this case, as shown in FIG. 8, $P_+(\theta, \phi)$ is shifted along the direction of $\theta$ by $2\pi$. Given the periodic property of the view angle, the original front beam data and its shifted version are equivalent. Therefore, one can combine the original back beam with the shifted version of the front beam. To do this, one redefines the original back beam as the new front beam and the shifted version of the front beam as the new back beam. The new offset is now defined as $\Delta = 2\pi - 2p\pi$, and one has $0 < \Delta < \pi - 2\phi_m$ for $\frac{1}{2}\phi_m/\pi < p < 1$.

DETAILED DESCRIPTION OF THE INVENTION

Figure 1:
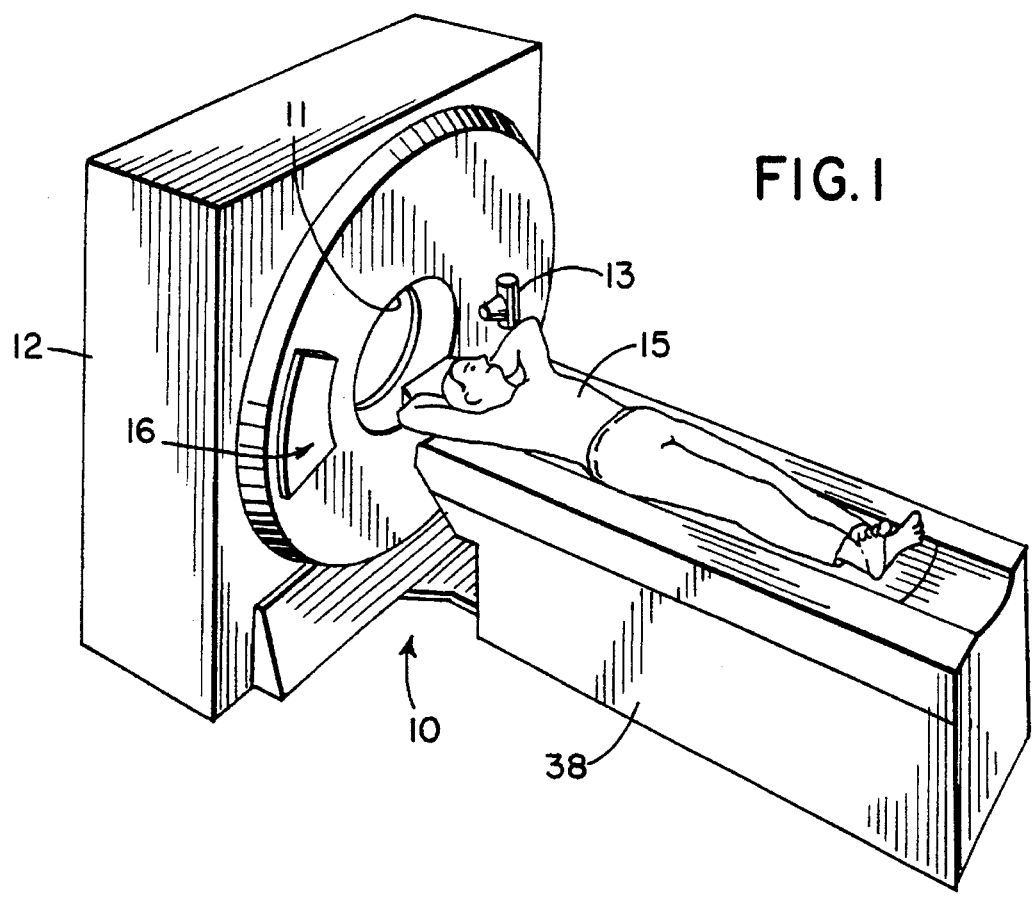
FIG. 1 is a pictorial view of a CT imaging system in which the present invention may be employed.
Figure 2:
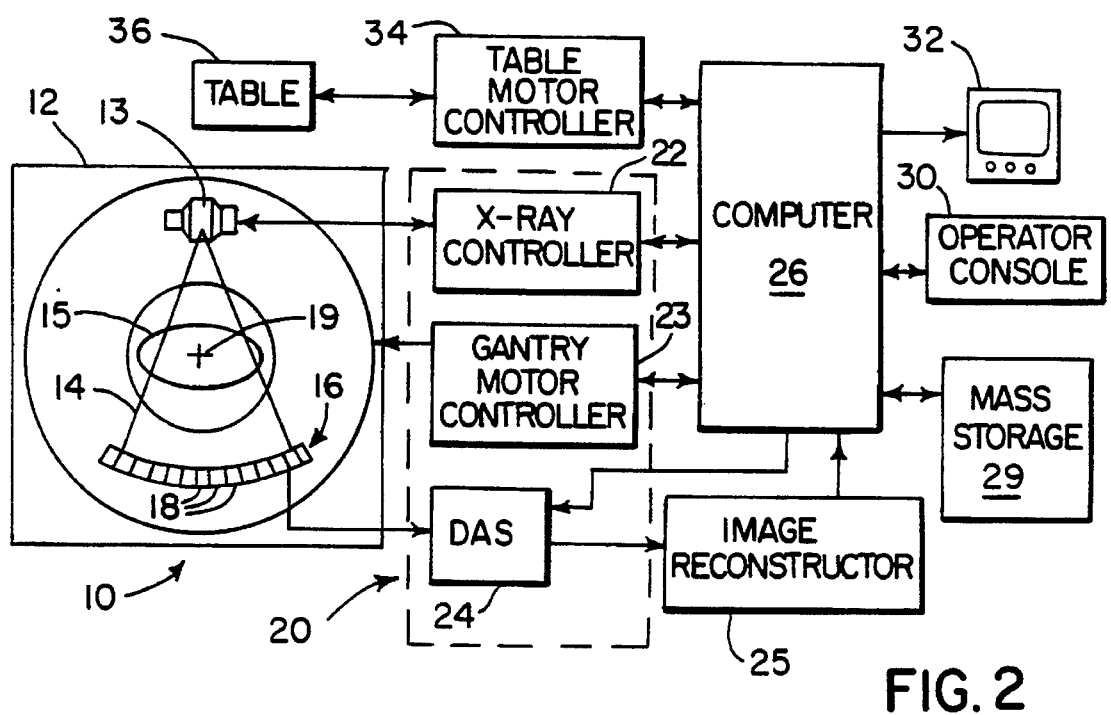
FIG. 2 is a block schematic diagram of the CT imaging system.

With initial reference to FIGS. 1 and 2, a computed tomography (CT) imaging system 10 includes a gantry 12 representative of a "third generation" CT scanner. Gantry 12 has an x-ray source 13 that projects a beam of x-rays 14 toward a detector array 16 on the opposite side of the gantry. The detector array 16 is formed by two rows of detector elements 18 which together sense the projected x-rays that pass through a medical patient 15. Each detector element 18 produces an electrical signal that represents the intensity of an impinging x-ray beam and hence the attenuation of the beam as it passes through the patient. During a scan to acquire x-ray projection data, the gantry 12 and the components mounted thereon rotate about a center of rotation 19.

The rotation of the gantry and the operation of the x-ray source 13 are governed by a control mechanism 20 of the CT system. The control mechanism 20 includes an x-ray controller 22 that provides power and timing signals to the x-ray source 13 and a gantry motor controller 23 that controls the rotational speed and position of the gantry 12. A data acquisition system (DAS) 24 in the control mechanism 20 samples analog data from detector elements 18 and converts the data to digital signals for subsequent processing. An image reconstructor 25, receives sampled and digitized x-ray data from the DAS 24 and performs high speed image reconstruction according to the method of the present invention. The reconstructed image is applied as an input to a computer 26 which stores the image in a mass storage device 29.

The computer 26 also receives commands and scanning parameters from an operator via console 30 that has a keyboard. An associated cathode ray tube display 32 allows the operator to observe the reconstructed image and other data from the computer 26. The operator supplied commands and parameters are used by the computer 26 to provide control signals and information to the DAS 24, the x-ray controller 22 and the gantry motor controller 23. In addition, computer 26 operates a table motor controller 34 which controls a motorized table 36 to position the patient 15 in the gantry 12.

Figure 7:
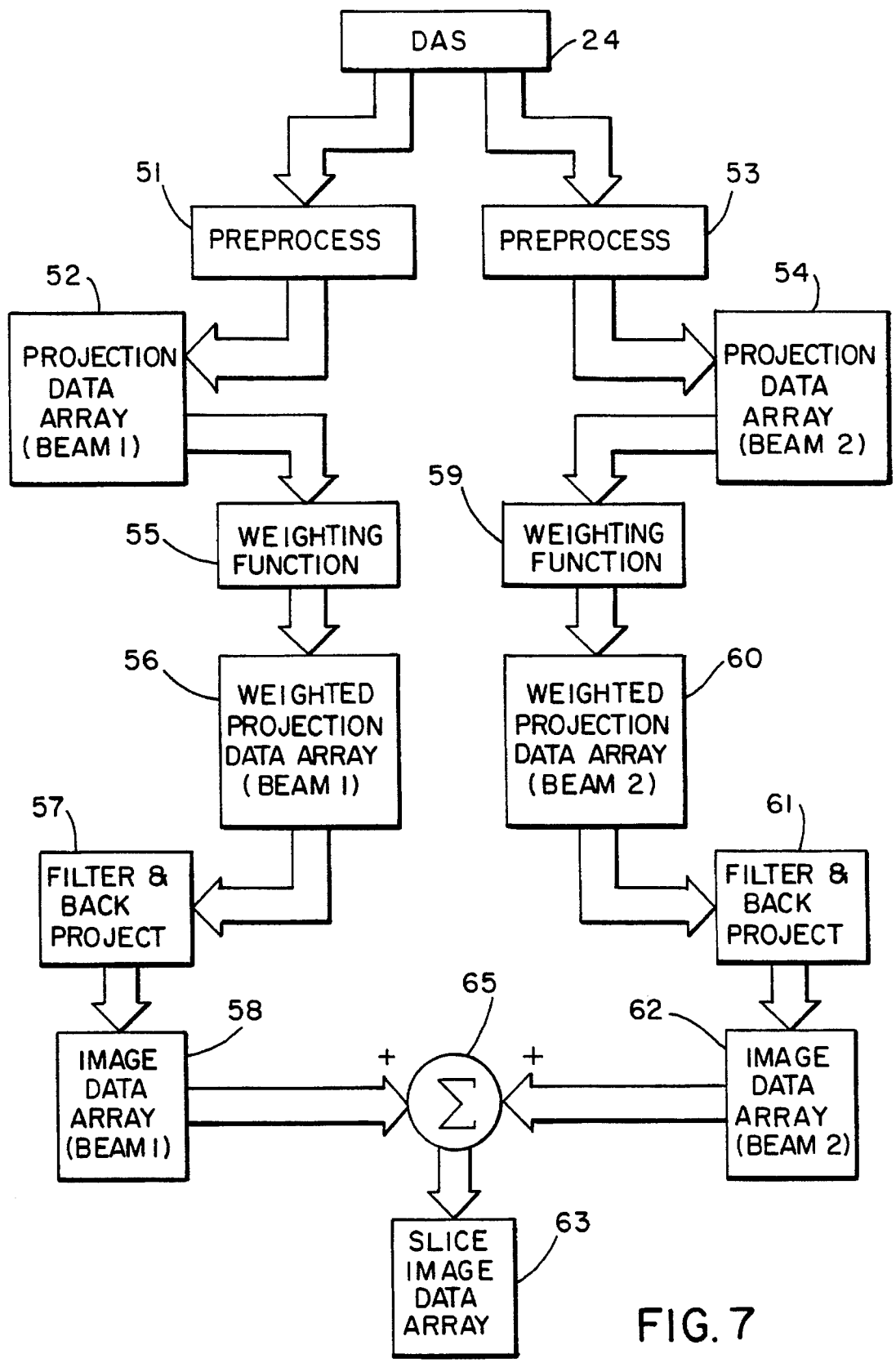
FIG. 7 is a block diagram of an image reconstructor which forms part of the CT imaging system of FIG. 2.

The present invention is implemented in the image reconstructor 25 which is shown in more detail in FIG. 7. Each view of data from the DAS 24 for the first fan beam is received at 51 where it is preprocessed to correct for various well-known errors such as beam hardening, offsets and variations in detector and channel gain. Also, the negative logarithm is taken to provide projection data which is stored in a projection data array 52. The same preprocessing is applied to the second fan beam scan data at 53 and it is stored in a projection data array 54. It is the projection data stored in arrays 52 and 54 which is combined according to the present invention to produce a slice image.

Referring still to FIG. 7, the right set of projection data in the beam 1 array 52 is read out and the corresponding weighting function indicated above in equation (9) is applied at 55. The weighted projection data is written into the corresponding location in an array 56, and this weighted projection data is filtered and back projected in a standard manner at 57 to produce a beam 1 image data array 58. Similarly, the corresponding data set of beam 2 is read out of array 54 and the corresponding weighting function indicated above in equation (9) is applied at 59. The resulting weighted projection data array 60 is filtered and back projected at 61 to produce a second beam image data array 62.

A slice image at location $z_s$ is produced at 63 by combining the two image arrays 58 and 62. This is accomplished by summer 65 which adds the magnitude of each pixel in beam 1, array 58 with the magnitude of the corresponding pixel in the beam 2, array 62. The resulting slice image array 63 may be stored for later use or displayed to the operator.

Many variations can be made from the preferred embodiment without departing from the spirit of the invention. For example, the filtering and back projection may be performed first on one beam and then the other beam rather than in parallel as described. Also, it is possible to combine the weighted projection data in arrays 56 and 60 prior to filtering and back projection. The invention is also applicable to fourth generation CT scanners.

I claim:

1. A method of producing a tomographic image of an object from projection data acquired in a helical scan, the data derived from a pair of x-ray fan beams disposed along a z axis and each producing a series of fan beam projections at a plurality of gantry angles θ about the z axis and each fan beam projection subtending an angle φ, the steps comprising:

a) acquiring a set of projections over gantry angles θ ranging over 180° +φ as the imaged object is translated along the z axis, the set of projections forming a first data array indicating the attenuation of x-ray energy in the first fan beam by the object, and forming a second data array indicating the attenuation of x-ray energy in the second fan beam by the object;

b) multiplying the data in the first data array by a first set of weighting values;

c) multiplying the data in the second data array by a second set of weighting values;

d) combining the corresponding weighted data in the first and second data arrays;

e) producing the tomographic image from the combined first and second data arrays.

2. The method as recited in claim 1 in which the weighted data in said first and second data arrays are separately filtered and back projected prior to being combined.

3. The method as recited in claim 1 in which each of said first and second data arrays are divided into a plurality of regions and the weighting values employed in steps b) and c) are determined in part by which of said plurality of regions the data being multiplied resides.

4. The method as recited in claim 3 in which each of said first and second data arrays are divided into five regions.

* * * * *